United States Patent [19]

Nissen

[11] Patent Number: 4,582,092

[45] Date of Patent: Apr. 15, 1986

[54] TUBE TO BE FED INTO A PIPELIKE CAVITY

[76] Inventor: Richard B. Nissen, DK-8870 Langaa, Denmark

[21] Appl. No.: 651,658

[22] Filed: Sep. 18, 1984

Related U.S. Application Data

[63] Continuation of Ser. No. 468,055, filed as PCT DK82/00054, Jun. 14, 1982, published as WO82/04472, Dec. 23, 1982, § 102(e) date Feb. 15, 1983, abandoned.

[30] Foreign Application Priority Data

Jun. 15, 1981 [DK] Denmark ............................ 2592/81

[51] Int. Cl.⁴ .............................................. F16L 58/02
[52] U.S. Cl. .................................... 138/109; 138/103; 138/137; 138/140; 138/178; 156/287
[58] Field of Search ............... 138/103, 109, 137, 140, 138/178; 156/287; 264/269; 128/349 R

[56] References Cited

U.S. PATENT DOCUMENTS

| | | | |
|---|---|---|---|
| 3,050,786 | 8/1962 | St. John et al. | 264/269 X |
| 3,948,290 | 4/1976 | Arisland | 138/109 |
| 4,043,345 | 8/1977 | Kramann et al. | 128/349 R |
| 4,109,659 | 8/1978 | Sheridan | 128/349 R |
| 4,188,979 | 2/1980 | Nakamura et al. | 138/109 |
| 4,368,091 | 1/1983 | Ontsuga et al. | 264/269 X |

FOREIGN PATENT DOCUMENTS 47-901  9/1972  Japan .................................. 264/260

*Primary Examiner*—James E. Bryant, III
*Attorney, Agent, or Firm*—Stevens, Davis, Miller & Mosher

[57] ABSTRACT

Tube to be introduced in a pipelike cavity, and where the forward end of the tube is secured to the entrance to this cavity, and the following part of the tube is introduced through this forward end by a turning inside out, and where the tube to facilitate this operation in its internal layer, which after the introducing turns outside, has build-in compression stresses and/or in its outer layer, which after introducing turns inward, has build-in tension stresses.

2 Claims, 1 Drawing Figure

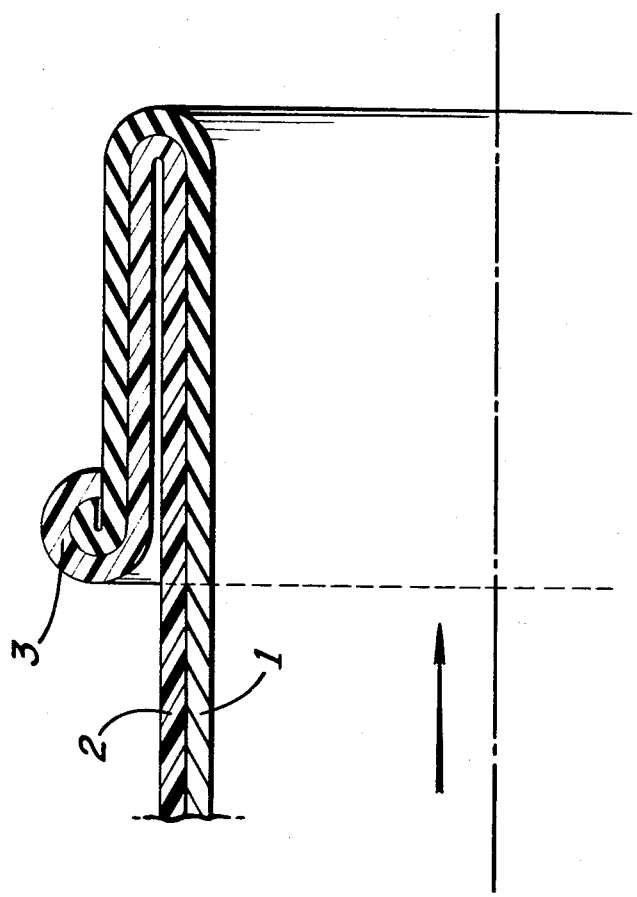

TUBE TO BE FED INTO A PIPELIKE CAVITY

This application is a continuation, of application Ser. No. 468,055, filed as PCT DK82/00054, Jun. 14, 1982, published as WO82/04472, Dec. 23, 1982, § 102(e) date filed Feb. 15, 1983, now abandoned.

BACKGROUND OF THE INVENTION

1. Field of the Invention

The present invention relates to a tube to be fed into a pipelike cavity, f.inst. to carrying out endoscopi or other surgical treatment, where a tube has to be fed into the body. According to the invention the tube may also be used as an internal lining of a pipeline in general and especially to stop up a leakage in a pipeline, which for some reasons is difficult accessible from the outside, and where it may be difficult to localize the leakage, as f.inst. pipelines surrounded by an insulation or pipelines placed underground, or generally where it is desired to provide a pipeline with an internal lining of a relatively elastic material.

2. Description of the Prior Art

It is known f.inst. from British Pat. No. 1 534 441 to introduce a flexible tube into a pipe by turning the tube inside out by creating a pressure differential between the opposite side of the turned-over section of the flexible tube, which involves the use of devices that under certain circumstances are rather inconvenient.

SUMMARY OF THE INVENTION

It is an object of the present invention to avoid or substantially diminish these pressure devices for introducing the tube.

This is obtained according to the invention by using a tube having at least two layers, of which the original inside-layer, which after insertion is turned outside, is provided with stresses of compression, and the original outside-layer, which after insertion turns inward, is provided with stresses of tension.

It is obvious that these stresses may be produced when a tube is turned inside out, but as these stresses will disappear when this tube is again turned inside out by the introducing according to the invention, the stresses produced in this way are too weak to obtain the desired effect.

It will be understood that for carrying out this introducing operation, it is necessary that the tube consists of a substantially elastic and flexible material, as f.inst. rubber or plastic with corresponding property.

These stresses have the effect that, when the turned-over forward end of the tube is engaged at the entrance to the pipeline cavity, it will be possible to feed the following part of the tube through this portion and fill up the cavity without the use of any or only a small amount of mechanical forces.

It is a further advantage by using this kind of tube that during its introducing no relative movement will appear between the tube and the inside wall of the cavity, so that by its use to endoscopi inconveniences and pains during the introducing are avoided, and by introducing of a tightning thin-walled tube in a pipeline the possibility of the tube being damaged by rugness in the pipe is avoided.

To obtain the opposite directed stresses in the tube, this may according to the invention preferably constitutes a laminate with at least two layers.

If for instance the tube consists of rubber, it may be produced by gluing together two concentric within each other placed rubber tubes, of which the one is tensioned and the other compressed during the gluing operation.

Preferably, according to the invention said compression-and/or tension-stresses may be transversed to the longitudinal direction of the tube. Hereby is obtained that the stresses provided in the material of the tube in its at any time forward end during the introducing in an effective way will promote the turning inside out action and speed up the introducing of the tube in the pipelike cavity.

Furthermore, according to the invention the tube can be made of a plastic material, where the stresses in question are frozen-in, so that the stresses may be liberated and activated by suitable warming up of the introducing end of the tube. In this case it may be suitable to arrange the molecular structure of the plastic material in such a way that the frozen-in stresses are substantially transvers to the longitudinal direction of the tube. In carrying out the introducing operation an electrical heating element may be used, which is displaceable within the tube and during the introducing operation continuously will be placed at the forward end of the tube, where the turning-over is taking place. This may for instance be obtained by guiding means which ensure that the heating element is moving forward with a speed being exactly one half of that for the tube. When the introducing operation has terminated, the heating element may be removed by pulling it backward through the tube.

If the pipelike cavity is not rectlinear, it may especially at points where relatively sharp corners appear, be advantageous to provide that surface of the tube, which after introducing is turned outside, with grooves or other sort of rugged surface, which increases the friction in order to prevent displacement of the tube in relation to the pipe during its further introducing.

In order to facilitate the state of the introducing operation the turned-over forward end of the tube may be provided with a bead to secure the forward end at the entrance to the pipelike cavity.

BRIEF DESCRIPTION OF THE DRAWING

The invention will now be described by way of an embodiment with reference to the accompanying drawing, which schematically shows a section through the forward end of the tube according to the invention before its introduction in a pipelike cavity, and where for the sake of clarity the wall-thickness is shown exaggerated in relation to the diameter of the tube.

DESCRIPTION OF THE PREFERRED EMBODIMENTS

By the embodiment described the tube consists of two layers, namely one internal layer 1, which after the introduction of the tube in the pipelike cavity will turn outwards, and an outer layer 2, which after the introduction turns inwards. The two layers are mutually connected by means of a suitable adhesive.

By producing of the tube, and especially by the gluing of the two layers the internal layer 1 is compressed and the outer layer 2 is tensioned, so that in the finished product there will be compressing stresses in the internal layer 1 and tension stresses in the outer layer 2, and preferably so that these stresses are substantially transversed to the longitudinal direction of the tube and of a magnitude greater than those produced by turning a tube inside out.

If the tube is made of rubber or a corresponding elastic material, this may be achieved thereby that for the outer layer 2 is used a tube with smaller diameter than the tube used for the internal layer 1.

If a plastic material is used, these stresses, in a way known per se, may be frozen in the material and will be activated when the tube is to be introduced in the cavity thereby, that the at any time forward end of the tube is locally warmed up for liberating of the frozen-in stresses. For this purpose may for instance as mentioned above an electrical heating element be used, which is easily displaceable within the tube.

For endoscopi or other surgical application may possibly be used a plastic material of the kind, where the frozen-in stresses will be liberated by the body temperature.

During the introducing of the tube its forward turned-over end must be maintained at the entrance of the pipelike cavity, and this end of the tube may for this purpose be provided with a bead 3 or other means for holding the forward end.

As mentioned above the tube may consist of two layers, of which at least one is provided with the necessary build-in stresses, and possibly there may between these two layers be arranged a stress-free layer of a special deformable material.

When using a plastic material it will also be possible to use only one layer, when by an appropriate method of manufacturing the build-in stresses will only be present in the outer parts of the wall.

Owing to the stresses, which according to the invention are built into the wall of the tube, the introducing into the pipelike cavity may be achieved without or with rather small auxiliary forces, which owing to the circumstances may be pneumatic, hydraulic or mechanical, and it may be obtained in different ways depending on the length of the tube.

I claim:

1. A tube having an inside layer and outside layer and a turned-over forward end to be fed into a pipelike cavity, said forward end of the tube has a bead thereon to hold stationary said end during introduction of said tube into the pipelike cavity, said inside layer has built-in compression stresses and said outside layer has built-in tension stresses said compression and/or tension stresses are substantially transverse to the longitudinal direction of the tube, which wall stresses upon turning inside out and outside in aid in the introduction of the tube into the pipelike cavity.

2. Tube as defined in claim 1, which consists of an adequate plastic material, wherein the said stresses are frozen-in, so as to be liberated by adequate warming up during introducing of the tube.

* * * * *